US009600849B2

(12) United States Patent
Ebner et al.

(10) Patent No.: US 9,600,849 B2
(45) Date of Patent: Mar. 21, 2017

(54) PROVIDING MULTIPLE ROLES IN COMPUTER-IMPLEMENTED WORKSPACES

(71) Applicants: Rachel Ebner, Ra'anana (IL); Orly Bleier, Hod Hosharon (IL); Avihai Tamari, Natanya (IL); Ida Shemesh, Ra'anana (IL); Lea Kritchker, Ra'anana (IL)

(72) Inventors: Rachel Ebner, Ra'anana (IL); Orly Bleier, Hod Hosharon (IL); Avihai Tamari, Natanya (IL); Ida Shemesh, Ra'anana (IL); Lea Kritchker, Ra'anana (IL)

(73) Assignee: SAP Portals Israel Ltd., Ra'anana (IL)

( * ) Notice: Subject to any disclaimer, the term of this patent is extended or adjusted under 35 U.S.C. 154(b) by 653 days.

(21) Appl. No.: 13/795,892

(22) Filed: Mar. 12, 2013

(65) Prior Publication Data

US 2014/0282024 A1 Sep. 18, 2014

(51) Int. Cl.
*H04L 29/06* (2006.01)
*G06Q 50/22* (2012.01)
*G06Q 10/10* (2012.01)

(52) U.S. Cl.
CPC ........... *G06Q 50/22* (2013.01); *G06Q 10/103* (2013.01); *H04L 63/10* (2013.01)

(58) Field of Classification Search
CPC ..................................................... H04L 63/10
See application file for complete search history.

(56) References Cited

U.S. PATENT DOCUMENTS

| | | | |
|---|---|---|---|
| 6,023,765 A | 2/2000 | Kuhn | |
| 6,202,066 B1 | 3/2001 | Barkley et al. | |
| 6,453,353 B1 | 9/2002 | Win et al. | |
| 6,754,885 B1 * | 6/2004 | Dardinski et al. | 717/113 |
| 7,441,239 B2 | 10/2008 | Bittner et al. | |
| 7,653,688 B2 | 1/2010 | Bittner | |
| 7,849,175 B2 | 12/2010 | Beringer et al. | |
| 7,873,942 B2 | 1/2011 | Shaburov et al. | |
| 8,291,214 B2 | 10/2012 | Helfman et al. | |
| 8,429,540 B1 | 4/2013 | Yankovich et al. | |
| 8,464,161 B2 | 6/2013 | Giles et al. | |
| 8,543,926 B2 | 9/2013 | Giles | |
| 2002/0147801 A1 * | 10/2002 | Gullotta et al. | 709/223 |

(Continued)

OTHER PUBLICATIONS

U.S. Appl. No. 13/597,632, filed Aug. 29, 2012, entitled "Enterprise Workspaces Externalization"; 32 pages.

(Continued)

*Primary Examiner* — Jason C Chiang
(74) *Attorney, Agent, or Firm* — Fish & Richardson P.C.

(57) ABSTRACT

Providing multiple roles in computer-implemented workspaces. When a first computer workspace in which a user has been assigned a first role and a second role is accessed, a first subset of content defined by the first role and a second subset of content defined by the second role can be made accessible to the user. Input to switch access from the first computer workspace to a second computer workspace that is different from the first computer workspace and in which the user is assigned only the second role can be received. In response, only the second subset of content can be provided to the user and access to the first subset of content can be prohibited.

17 Claims, 6 Drawing Sheets

(56) References Cited

U.S. PATENT DOCUMENTS

| | | |
|---|---|---|
| 2003/0105742 A1 | 6/2003 | Boreham et al. |
| 2003/0204433 A1* | 10/2003 | Botscheck et al. ............... 705/9 |
| 2007/0150300 A1* | 6/2007 | Fukazawa et al. ............... 705/1 |
| 2007/0180498 A1* | 8/2007 | Choudhary et al. .............. 726/4 |
| 2008/0140474 A1 | 6/2008 | Yu et al. |
| 2008/0189654 A1* | 8/2008 | Thomas ........................ 715/805 |
| 2009/0024609 A1* | 1/2009 | Barker et al. ..................... 707/5 |
| 2010/0275130 A1* | 10/2010 | McBride ....................... 715/751 |
| 2011/0162059 A1 | 6/2011 | Helfman et al. |
| 2011/0162074 A1 | 6/2011 | Helfman et al. |
| 2011/0231592 A1 | 9/2011 | Bleier et al. |
| 2011/0276914 A1* | 11/2011 | Ahlgren ................. G06F 9/468 715/771 |
| 2012/0023223 A1* | 1/2012 | Branch ................ G06F 9/4856 709/224 |
| 2012/0096408 A1 | 4/2012 | Boss et al. |
| 2013/0124807 A1* | 5/2013 | Nielsen et al. ............... 711/162 |
| 2013/0227440 A1* | 8/2013 | Chandra et al. ............. 715/760 |
| 2014/0019507 A1 | 1/2014 | Slakman et al. |
| 2014/0040178 A1 | 2/2014 | Sherman et al. |
| 2014/0136531 A1* | 5/2014 | Aflalo ................ G06F 17/3089 707/728 |
| 2014/0282024 A1 | 9/2014 | Ebner et al. |

OTHER PUBLICATIONS

U.S. Appl. No. 13/660,698, filed Oct. 25, 2013 entitled "Multiple User Interface Platform Support for Portal Applications", 42 pages.

U.S. Appl. No. 13/760,300, filed Feb. 6, 2013 entitled "Synchronizing User Relationship Across Computer Systems Implementing Workspaces", 40 pages.

* cited by examiner

| 202 — USER X | WORKSPACE ID 1 | DOCTOR | 214 |
| 204 — USER Y | WORKSPACE ID 2 | DOCTOR, PATIENT | 216 |
| 206 — USER Z | WORKSPACE ID 3 | PATIENT | 218 |

PROVIDING MULTIPLE ROLES IN COMPUTER-IMPLEMENTED WORKSPACES

TECHNICAL FIELD

The present disclosure relates to software, computer systems, and computer-implemented media for implementing workspaces in computer systems.

BACKGROUND

Enterprise Workspace (EWS) technology leverages existing enterprise portal (EP) capabilities and acts as an "add-on" to EP technology. For example, EWS user interface (UI) technology can run on top of existing EP technology. EWS functionality can provide a flexible, intuitive environment for single EWS users or groups of EWS users (or both) to create, integrate, organize, compose, modify, and delete content, through the use of modules, both structured and unstructured, on EWS pages within an EWS. EWS technology can allow EWS users to take advantage of a "self-service" approach that is a decentralized approach in assembling content on EWS pages, often without involvement by an enterprise's information technology group.

An EWS, therefore, is a central point where multiple EWS users can share content. Each EWS user can receive permission to access the EWS, and the content in the EWS. Each EWS user can be assigned permissions and roles that, in conjunction with a permission/role policy, can determine the content that each EWS user can access in the EWS. In some situations, an EWS user can be assigned a global role with respect to the EWS. In such situations, however, the EWS user may not be able to participate in the EWS in a role other than the global role that has been assigned to the user.

SUMMARY

The present disclosure involves systems, software, and computer-implemented methods for providing multiple roles in computer-implemented workspaces.

In general, one innovative aspect of the subject matter described here can be implemented as a method performed by data processing apparatus. A first computer workspace in which a user has been assigned a first role and a second role is identified. Each of the first computer workspace and the second computer workspace provides content. At least a portion of the content is accessible by the user. The first role defines a first subset of the content that is accessible by the user. The second role defines a second subset of the content that is accessible by the user. It is determined that the user has accessed the first computer workspace in which the user has been assigned the first role and the second role. The first subset of the content and the second subset of the content is provided to the user in response to determining that the user has accessed the first computer workspace.

This, and other aspects, can include one or more of the following features. The content can include data and computer-implemented applications accessible by the user. A first relationship and a second relationship between the user and the first computer workspace can be persisted. The first relationship and the second relationship can be based on the first role and the second role, respectively. Persisting the first relationship can include tagging the first relationship with a string of characters that represents the first role. Persisting the first relationship can include persisting the first relationship in the first computer workspace. Persisting the second relationship can include persisting the second relationship in a user account associated with the user. Persisting the first relationship can include associating an identifier to identify the user and an identifier to identify the first computer workspace with the first role. Determining that the user has accessed the first computer workspace can include receiving a selection of the first computer workspace in a user interface that displays the first computer workspace and a second computer workspace that is different from the first computer workspace. The user can be assigned only the second role in the second computer workspace. In response to receiving a selection of the second computer workspace in the user interface, a different user interface that provides only the second subset of the content can be displayed. In the user interface, an input to switch from the first computer workspace to the second computer workspace can be received. A different user interface that displays the second subset of content can be displayed in response to receiving the input to switch. Determining that the user has accessed the first computer workspace can include automatically and without user intervention determining that the user has accessed the first computer workspace when the user accesses a computer system that provides the workspaces. Automatically and without user intervention, determining that the user has accessed the first computer workspace can include determining that the user has accessed the first computer workspace based on factors including a geographical location from which the user accesses the first computer workspace or the time of day.

Another innovative aspect of the subject matter described here can be implemented as a computer-readable medium storing instructions executable by data processing apparatus to perform the operations described here or a system that includes data processing apparatus and the computer-readable medium (or both).

A further innovative aspect of the subject matter described here can be implemented as a system that includes data processing apparatus and a computer-readable medium storing instructions executable by the data processing apparatus to perform operations. The operations can include determining access of a first computer workspace in which a user has been assigned a first role and a second role. The first computer workspace provides content at least a portion of which is accessible to the user. The first role and the second role define a first subset and a second subset, respectively, of the content that is accessible by the user. The operations include providing the first subset of the content and the second subset of the content to the user in response to determining the access of the first computer workspace. The operations include receiving input to switch access from the first computer workspace to a second computer workspace that is different from the first computer workspace. The user is assigned only the second role in the second computer workspace. The operations include providing the second subset of the content and prohibiting access to the first subset of the content in response to receiving the input to switch the access from the first computer workspace to the second computer workspace.

This, and other aspects, can include one or more of the following features. Determining the access of the first computer workspace can include automatically and without user intervention determining that the user has accessed the first computer workspace. Automatically and without user intervention determining that the user has accessed the first computer workspace can include automatically and without user intervention determining that the user has accessed the first computer workspace based on factors including a geographical location from which the user accesses the computer workspace or the time of day.

Another innovative aspect of the subject matter described here can be implemented as a computer-readable medium storing instructions executable by data processing apparatus to perform the operations described here or a computer-implemented method performed by data processing apparatus (or both).

While generally described as computer-implemented software embodied on tangible media that processes and transforms the respective data, some or all of the aspects may be computer-implemented methods or further included in respective systems or other devices for performing this described functionality. The details of these and other aspects and implementations of the present disclosure are set forth in the accompanying drawings and the description below. Other features and advantages of the disclosure will be apparent from the description and drawings, and from the claims.

BRIEF DESCRIPTION OF THE DRAWINGS

Like reference numbers and designations in the various drawings indicate like elements.

DETAILED DESCRIPTION

Figure 1:
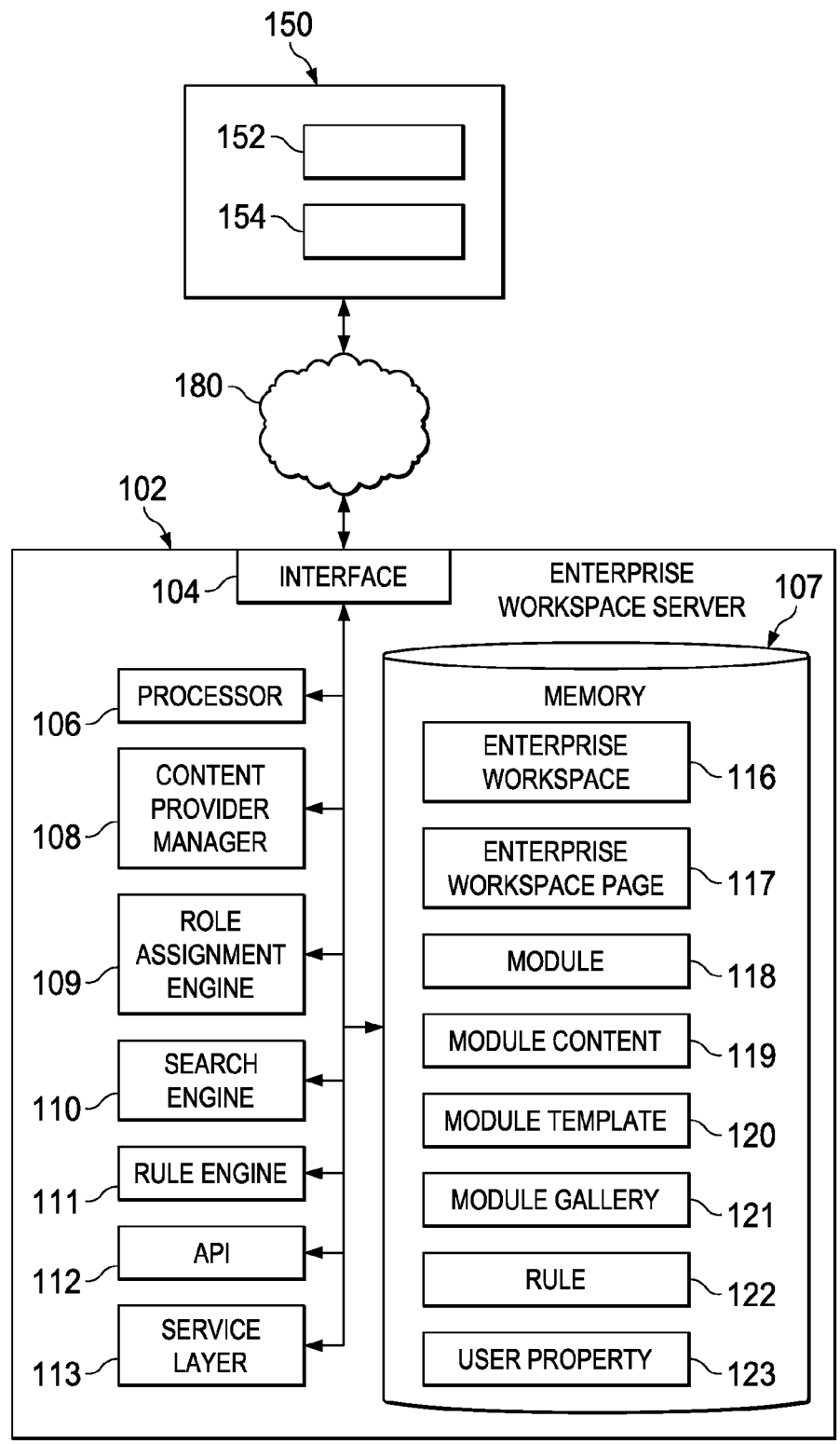
FIG. 1 illustrates an example of an example computer system connected to an example Enterprise Workspace Server.

A computer system can implement an external facing enterprise portal (EP) or a workspace that allows multiple users to access content that is available through the portal or the workspace. The workspace can be a collaboration component that resides on a computer system, for example, a frontend computer system, and exposes content, for example, specific business data, received from other computer systems such as backend computer systems. The workspace can assign multiple users permission to access the content of the workspace. Different users can be assigned different roles associated with respective permission levels. For example, a first user can be defined as a "Manager" who has permission to modify the workspace. A second user can be defined as a "Member" who has permission to view content but not to modify the workspace structure. A third user can be defined as an "Owner," who is similar to a "Manager," but additionally has permission to close the workspace or transfer ownership of the workspace to a different user (or both).

Often, the permission level associated with a user is derived from the user's role in the workspace. As described above, the first user, who has been defined as a "Manager," can modify content (for example, data and computer-implemented applications) provided by the workspace, while the second user, who has been defined as a "Member," can only view the content. In some situations, the computer system that provides the workspace can be a frontend computer system that is interconnected with backend computer systems. In such situations, the permission level of a user can be determined or derived from the permission level for the user in one or more of the backend computer systems, for example, because the permissions for content that arrives from a backend computer system may reside on the backend computer system. That is, there may be no relationship between the workspace level permission and the backend permission.

The workspace described above can be a generic workspace. In some cases, the workspace can be used as part of a specific business solution and can solve a specific business problem. Different users can access the same workspace; each user can be assigned a respective business-level role. Alternatively (or in addition), the same user can access two (or more) different workspaces. In a first of the two workspaces, the user can be assigned a role that is different from a role in a second of the two workspaces. In sum, the same user can have different business-level roles in different workspaces. In such cases, the roles assigned to the same user in the different workspaces can be distinguished when assigning business-levels roles to the user in each of the different workspaces.

One way to assign the same business-level role to a user in multiple workspaces is to assign a global role to the user. Such system-wide roles exist in many systems. For example, the user can be a doctor of multiple patients, each of whom is associated with a respective workspace. In this example, different patients are associated with the same doctor, who is helping each patient's recovery. Each patient is assigned a business-level role of "Patient" globally, and therefore when the user logs in to his assigned workspace, i.e., the workspace in which the user, as the patient, is at the center, he is indeed identified as the patient. The same doctor, who is helping all of the different patients, is assigned a global business-level role of "Doctor" that is common to all the workspaces. A globally assigned business-level role is one which applies to all workspaces. A workspace-level role, in contrast, is one which applies to a specific workspace.

A problem with this flow is that once the user has been assigned a particular business role globally, the user may not be able to participate in the workspace (or in other workspaces) under a different role. For example, if the user is marked as a "Doctor" in one of the backend computer systems, then the user is assigned the global role of "Doctor" in frontend and other related computer systems that implement respective workspaces. Consequently, in all workspaces in which the user is a member, the user will only have access to content available to a user assigned the role of "Doctor." The same user may not be able to be assigned more than one role—for example, a "Patient" role and a "Doctor" role—in the same workspace. For example, the user who has been assigned the global business-level role of "Doctor" may not be able to access any workspace as a "Patient." At any instant, the user can either be in the "Patient" role or in the "Doctor" role, but not both. Thus, the user can be a doctor in all workspaces in the system, but cannot have a workspace in which that same user is defined as a patient.

This disclosure describes solutions to the afore-described problems by providing multiple roles in computer-implemented workspaces. The techniques described below enable a single user to be assigned different business-level roles in the same workspace or in two or more different workspaces. For example, the user can be assigned a global business-level role across two or more different workspaces and can be assigned a specific business-level role, which is different from the global business-level role, in one of the two or more different workspaces. In the workspaces in which the user is assigned the global business-level role, the user can have access to a first subset of content, while, in the workspace in which the user is assigned the specific business-level role, the user can have access to a second subset of content. Depending on any global business-level role and the specific business-level role, the scope of the first subset can be greater than or less than the scope of the second subset. As described below with reference to the following figures, multiple permissions associated with the multiple roles can be represented and persisted correctly and have the scope of a single workspace. In addition, user interface patterns that support the user interaction for each of the multiple roles are defined.

FIG. 1 is an example of a computer system 150 connected to an example Enterprise Workspace Server 102. The EWS server 102 (described below) is an electronic computing device operable to implement an EWS and to receive, transmit, process, store, or manage data and information associated with the first computer system 104. The EWS server 102 allows EWS users to compose, modify, delete, and deploy EWS pages. Through a graphical user interface (GUI), a user of the EWS server 102 is provided with an efficient and user-friendly presentation of content provided by or communicated within the computer system 150.

The computer system 150 can be, for example, a desktop computer, a laptop computer, a personal digital assistant (PDA), a tablet computer, a smartphone, and the like. The computer system 150 can implement the techniques described in this disclosure as computer-readable instructions stored on a computer-readable medium 152 and executable by data processing apparatus 154. The computer system 150 can be connected to the EWS server 102 through one or more wired or wireless networks 180, for example, the Internet.

In some implementations, the computer system 150 can determine that a first role has been assigned to a user of a computer workspace that provides content. This role is applicable inside the context of this workspace. The workspace can include multiple users. Because of the role assignment to each user, at least a portion of the content provided by the workspace is accessible to each user. The first role assigned to the user can define a first subset of the content that is accessible by the user. For example, the computer workspace can be a contextual workspace to store and manage data associated with a patient by one or more doctors, one or more health care service providers, and the like. In this workspace, the patient can occupy a central role with which the roles assigned to the one or more doctors and the one or more health care service providers interact. The workspace can provide a subset of content to the patient, each doctor, and each health care service provider. The subset of content accessible to the patient may not be accessible by each doctor and each health care service provider. Similarly, the subset of content accessible to a health care service provider may not be accessible by the doctor and vice versa. Also, the subset of content accessible by one doctor may not be accessible to another doctor, for example, without the patient's consent.

The computer system 150 can determine that a second role has been added to the user. The second role can be different from the first role. For example, using the computer system 150, a user in the workspace with permission levels to add a new role (e.g., a "Manager" or "Owner") can add the second role. Alternatively, the user with permission levels to add a new role can create a new role for the user in the workspace of a computer system interconnected with the computer system 150, such as a backend computer system. The creation of the new role in the workspace of the backend computer system can result in an addition of the role to the workspace of the computer system 150. In some implementations, the second role assigned to the user can be added in a workspace that is different from the workspace in which the first role has been assigned to the user. In some implementations, the second role assigned to the user can be added can be the same as the workspace in which the first role has been assigned to the user.

As described above, the first role and the second role can be different from each other. Consequently, a scope of content accessible to the user in the first role can be different from a scope of content accessible to the user in the second role. Similarly to the first subset of content defined as being accessible to the user in the first role, the second role assigned to the user can define a second subset of the content that is accessible by the user. The second subset can include content that is different from the first subset or can overlap at least partially with the first subset. The user can access the workspace under either the first role or the second role. When the user accesses the computer workspace, the computer system 150 can determine a role that is associated with the user. The computer system 150 can provide a subset of the content to the user in response to determining the role. If the user has accessed a workspace in which the user is assigned only the first role (for example, a "Doctor" role), then the computer system 150 can provide only the first subset. Conversely, if the user has accessed a different workspace in which the user is assigned only the second role (for example, a "Patient" role), then the computer system 150 can provide only the second subset. If, on the other hand, the user has accessed a workspace in which the user is assigned both the first role (i.e., the "Doctor" role) and the second role (i.e., the "Patient" role), then the computer system 150 can provide both the first subset and the second subset.

One of the users who can access all the workspaces can be the doctor who provides medical services to multiple clients. To the doctor, the computer system 150 can assign a first role of "Doctor" which allows the doctor to manage (for example, view, add, delete, change) the medical information of the respective clients. The doctor can be the owner or the manager (or both) of all the workspaces. Other users who can access the workspaces can include the multiple patients, each of whom can access a respective workspace. To each of the patients, the computer system 150 can assign a second role of "Patient" which allows each client to manage (for example, view, add, delete, change) only the respective user's workspace, for example, information inside the workspace that was created to track the patient's medical information.

The doctor may manage her own medical information. To do so, the doctor can add (for example, create) a new workspace to the existing workspaces, and assign a role of "Patient" to herself in the scope of the added workspace. In one example situation, the computer system 150 can determine that, in the added workspace, the "Patient" role has been added to the doctor. In the "Patient" role, the doctor may be able to access some content provided by the workspace that the doctor cannot access in the other workspaces in the "Doctor" role. After having added the second role, the doctor can access the system that provides the multiple workspaces either in the "Doctor" role or in the "Patient" role. As the doctor, she can access any of the workspaces in which she provides medical services to patients, and as a patient, she can access only the workspace in which she has been associated the "Patient" role.

In another example situation, the computer system 150 can determine that, in the added workspace, both the "Patient" role and the "Doctor" role has been added to the doctor. In such situations, the doctor can access any of the workspaces as the doctor, and the added workspace as both the doctor and the patient. In some implementations, the computer system 150 can determine the role that is associated with the doctor when the doctor accesses one of the multiple workspaces. In the accessed workspace, if the role is only the "Doctor" role, then the computer system 150 can provide a subset of the content (i.e., data and computer-implemented applications) that only a user in the "Doctor" role can access. Conversely, in the accessed workspace, if the role is the "Patient" role, then the computer system 150 can provide a different subset of the content (i.e., data and computer-implemented applications) that only a user in the "Patient" role can access. In the accessed workspace, if the role is both the "Doctor" role and the "Patient" role, then the computer system 150 can provide a subset of the content that is accessible to a user in both the "Doctor" role and the "Patient" role.

Figures 2, 3:
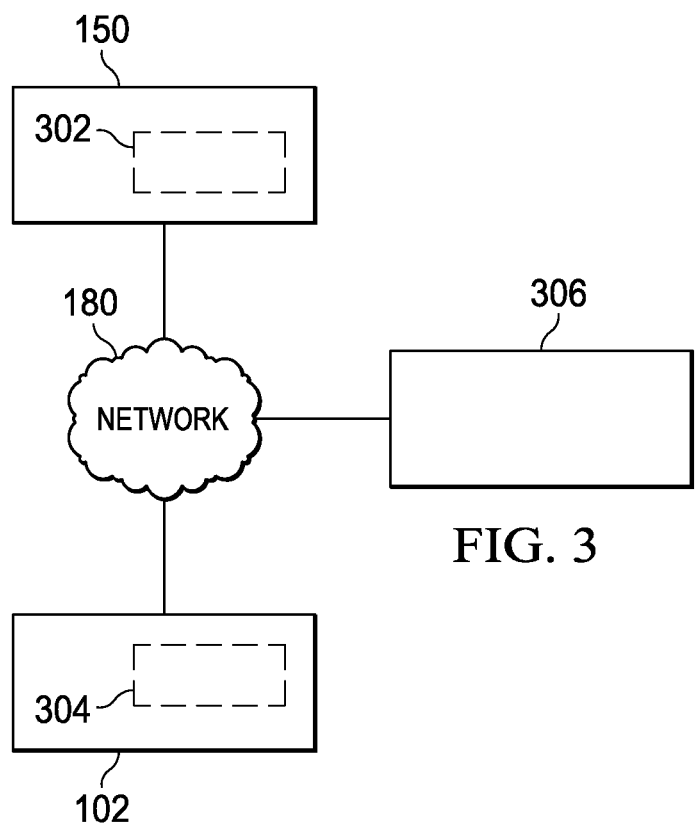
FIG. 2 is an example of marking one or more roles defined for users of the workspace provided by the example computer system of FIG. 1.
FIG. 3 is an example of persisting the one or more roles defined for users of the workspace provided by the example computer system of FIG. 1.

FIG. 2 is an example of marking one or more roles defined for users of multiple workspaces implemented by the example computer system 150. As described above, the permissions associated with the different roles can be represented and stored correctly so that the same user can be assigned different business roles in different workspaces (and possibly, multiple business roles in one workspace). To do so, the computer system 150 can persist a first relationship and a second relationship between the user and the computer workspace. A relationship can be defined implicitly and can be evaluated as the result of the meaning of the workspace or the business role of each user in the workspace or combinations of them. The first relationship and the second relationship can be based on the first role and the second role, respectively. In addition to that, there are also relationships between users that derive from the specific user-workspace relationships. For example, the doctor's role as "Doctor" can result in a "Doctor-Patient" relationship between the doctor and each patient who is assigned the "Patient" role in the different workspaces. Each patient can have a "Patient-Doctor" relationship with the doctor who is assigned the "Doctor" role in the patient's workspace. In the workspace in which the doctor has two roles—"Doctor" and "Patient"—the doctor can have both a "Doctor-Patient" relationship and a "Patient-Doctor" relationship. The relationships described in this example are relationships between two users, which is derived from the users' relationships with the workspace. Another type of relationship is a user-workspace relationship. For example, where the doctor's role is globally defined as "Doctor" across multiple workspaces, the doctor's relationship with each workspace is that of "Doctor." Where a patient's role is specifically defined as "Patient" in a certain workspace, then the patient's relationship with that workspace is "Patient." As described here, in some situations, the doctor can have a "Doctor" relationship and a "Patient" relationship with the same workspace or with different workspaces.

In some implementations, the business role for each user in the context of a workspace can be marked and persisted (i.e., stored), for example, in a table. In the example table shown in FIG. 2, the first row includes a user X in cell 202 who has been assigned "Workspace ID 1 " as a workspace identifier in cell 208. The relationship between the user X and the workspace can be tagged with a string of characters that represents user X's role in the workspace. For example, user X's role in the workspace has been tagged with a free-style text "Doctor" and stored in cell 214 of the first row. The second row includes a user Y in cell 204 who has been assigned "Workspace ID 2 " in cell 210. The relationship between the user X and the workspace has been tagged by two strings of characters in cell 216, namely, "Doctor" and "Patient." The third row includes a user Z in cell 206 who has been assigned "Workspace ID 3 " in cell 212. The relationship between the user Z and the workspace has been tagged by the free-style text "Patient" in cell 218.

The relationships described with reference to the table shown in FIG. 2 can be persisted in one or more of several locations. As shown in FIG. 3, the relationships can be persisted in the workspace as part of the workspace definition. In other cases, it can be persisted in an independent table inside a relational database on a computer-readable storage 302 in the computer system 150. Alternatively, the relationships can be persisted on the EWS server 102, for example, on a computer-readable storage 304. In some implementations, the relationships can be persisted on a separate computer-readable storage device 306 that is operatively coupled to the computer system 150 or the EWS server 102 or both through one or more wired or wireless networks 180, for example, the Internet. In some implementations, the relationships can be persisted as metadata on the user definition in the portal system (as additional metadata on the user) (not shown) using which the user accesses the workspace.

Persisting the relationships in the workspace can enable sharing the lifecycle of the workspace. When the workspace is deleted, all business roles of this workspace are also deleted. Persisting the relationships on the user account\user definition with which the user accesses the workspace can also enable sharing the lifecycle of the user. When the user's account is deleted, all of the user's business roles are also deleted. Persisting the relationship in a user account associated with the user can increase flexibility and allow complex searches. In such persistencies, an identifier is associated with the user to identify the user. Another identifier is associated with the workspace. Both identifiers are associated with the business role, all three of which are then stored.

Figure 4:
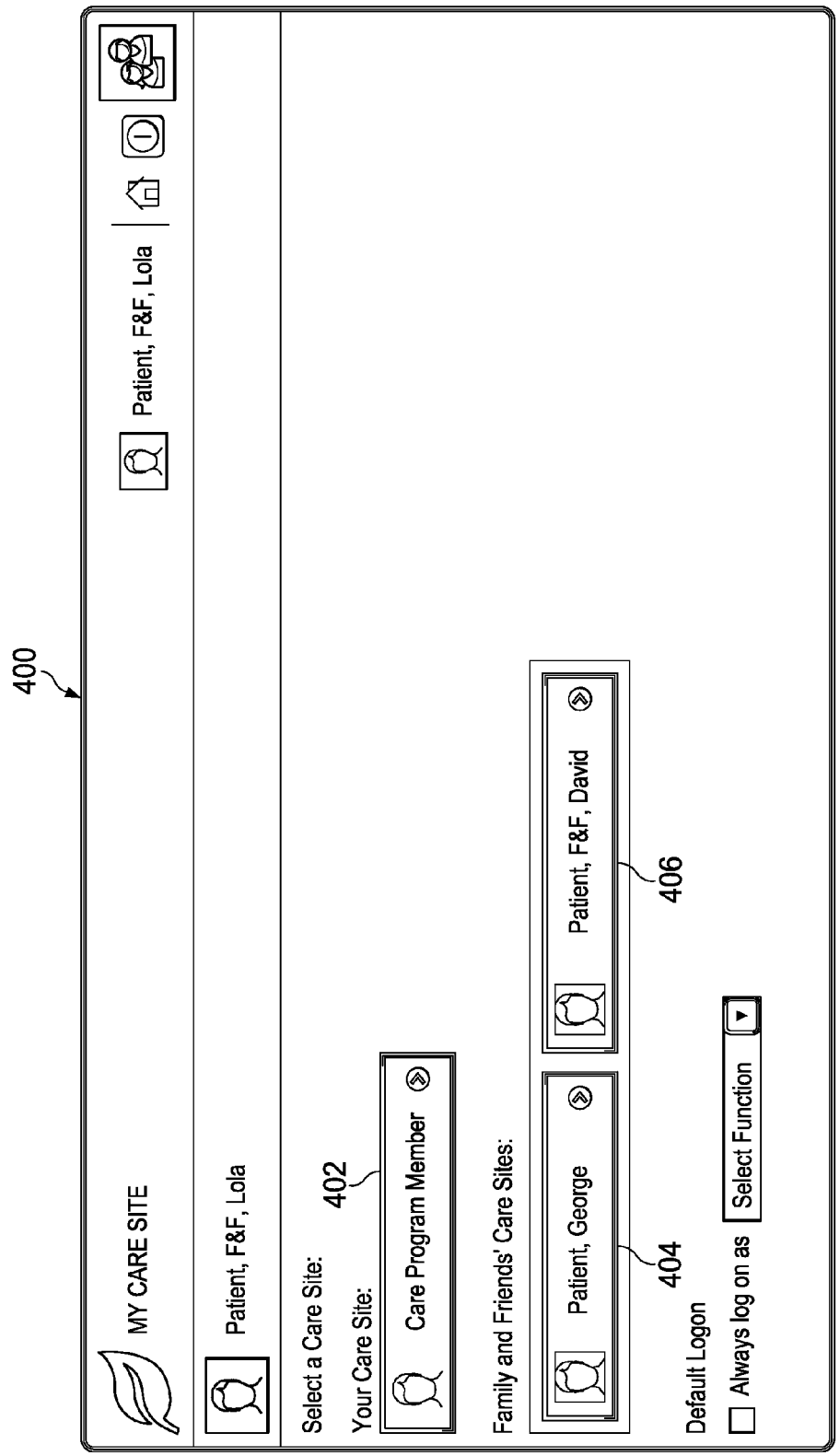
FIG. 4 is an example of a user interface to select a role in which the user can access the workspace.

FIG. 4 is an example of a user interface 400 to select a role in which the user can access the computer system that provides multiple workspaces. As described below, the user selects a role using the user interface 400 according to which the computer system allows the user to access a subset of content provided by a workspace based on the user's role in the workspace. The user interface 400 can be implemented as computer instructions stored on a computer-readable medium (for example, the computer-readable medium 152) and executable by data processing apparatus (for example, the data processing apparatus 154). For example, the user interface 400 can be implemented by the computer system 150. In some implementations, the computer system 150 can provide a user with a Uniform Resource Locator (URL) that references a webpage of a website. The webpage can be a landing page of the website from which the user can access the workspace provided by the computer system 150.

The example website 400 is a landing page of a website hosted by the computer system (for example, the computer system 150) that provides the workspaces that include content related to health care. The content can include data and applications associated with one or more care providers and one or more care receivers. Each care provider and each care receiver can have a workspace, to which other care providers or care receivers may have access. A care provider can provide care to one or more care receivers, and, consequently, can have access to each care receiver's workspace, where content associated with the care receiver is stored. A care receiver can have access only to his own workspace, where content associated with the care receiver, and not other care receivers, is stored. The example website 400 is the landing page for a first user entitled "Patient, F&F, Lola." The first user has been assigned two roles—a "Care Program Receiver" role and a "Care Program Provider" role—in either the same workspace or in two or more different workspaces. In a first workspace in which the first user is associated with the "Receiver" role, the first user has access to content associated with the first user. In a second workspace in which the first user is associated with the "Provider" role and George is associated with the "Patient, George" role, the first user has access to content associated with the second user. The scope of the content to which the first user has access in his role as the "Receiver" in the first workspace is different from the scope of the content to which the first user has access in his role as the "Provider" in the second workspace. Similarly to the second workspace, in a third workspace in which the first user is associated with the "Provider" role and David is associated with the "Patient, F&F, David" role, the first user has access to content associated with the third user.

In the user interface 400, the computer system 150 can display a first selectable object 402 (for example, a computer-selectable button), a second selectable object 404, and a third selectable object 406 associated with the first workspace, the second workspace, and the third workspace, respectively. The computer system 150 can present (for example, display) the user interface 400 on a display device connected to the computer system or to a client computer system that is connected to the computer system 150 or a backend computer system connected to the computer system 150. The first selectable object 402 can be associated with a first identifier (for example, a URL) that references the first workspace where a first subset of content provided to the first user in the "Care Program Receiver" role. In some implementations, the first user has the role of "Care Program Receiver" inside the first workspace only. The second selectable object 404 can be associated with a second identifier that references the second workspace where a second subset of content, which is associated with the second user and to which the first user in the "Care Program Provider" role has access. Thus, the first user is a member of the second workspace. Similarly, the third selectable object 404 can be associated with a third identifier that references a third workspace where a third subset of content, which is associated with the third user and to which the first user in the "Care Program Provider" role has access. The first user is a member of the third workspace as well. Additional selectable objects that correspond to additional roles can be displayed in the user interface 400.

When the first user accesses the user interface 400, the first user can select a selectable object that corresponds to a workspace. The computer system 150 can receive a selection of the workspace in the user interface 400. For example, if the user selects the first selectable object 402, then the computer system 150 can determine that the role associated with the user when the user accesses the first workspace is the "Care Program Receiver" role only. Similarly, if the user selects the second selectable object 402, then the computer system 400 can determine that the role associated with the user when the user accesses the second workspace is the "Care Program Provider" role. In a fourth workspace, the first user can be assigned both the "Care Program Provider" role and the "Care Program Receiver" role. The user interface 400 can include a fourth selectable object (not shown). If the user selects the fourth selectable object, then the computer system 150 can determine that the role associated with the user with the user accesses the fourth workspace is both the "Care Program Provider" role and the "Care Program Receiver" role.

As described above, each selectable object is associated with a workspace. that references a subset of content, and the logged-in user has a specific business role inside that workspace. In response to receiving the selection of the selectable object in the user interface 400, the computer system 150 can determine the respective role and display a different user interface in which the computer system 150 can provide the subset of content associated with the role. For example, if the first user selects the second selectable object 404, then the computer system 150 determines that the user has accessed the second workspace in a "Care Program Provider" role, specifically, for the second user entitled "Patient, George." In response, the computer system 150 presents (i.e., displays) the subset of content in the workspace that the first user has access to view in his "Care Program Provider" role for the second user entitled "Patient, George." In some implementations, the computer system 150 can present the user interface that is referenced by the identifier associated with the second selectable object 404.

The computer system 150 can enable the user to switch from a role in which the user has accessed the workspace to a different role. To do so, in some implementations, the computer system 150 can present a selectable object in the user interfaces that the computer system 150 displays to the user. In the user interface, the computer system 150 can detect a selection of the object. The selection is an input to switch from the first role, for example, the "Care Program Provider" role, to a second role, for example, the "Care Program Receiver" role. Alternatively, or in addition, the selection can be an input to switch from a first workspace in which the first user has a first role to a second workspace in which the first user has either a second role only or the first role and the second role. In response, the computer system 150 can display a different user interface that displays the second subset of the content. In some implementations, the selectable object that the user selects to switch from the first role to the second role can be associated with an identifier that references the second subset of the content. When the user switches from the first workspace to the second workspace, the computer system 150 can terminate the user's access to the workspace under the first role.

Figure 5:
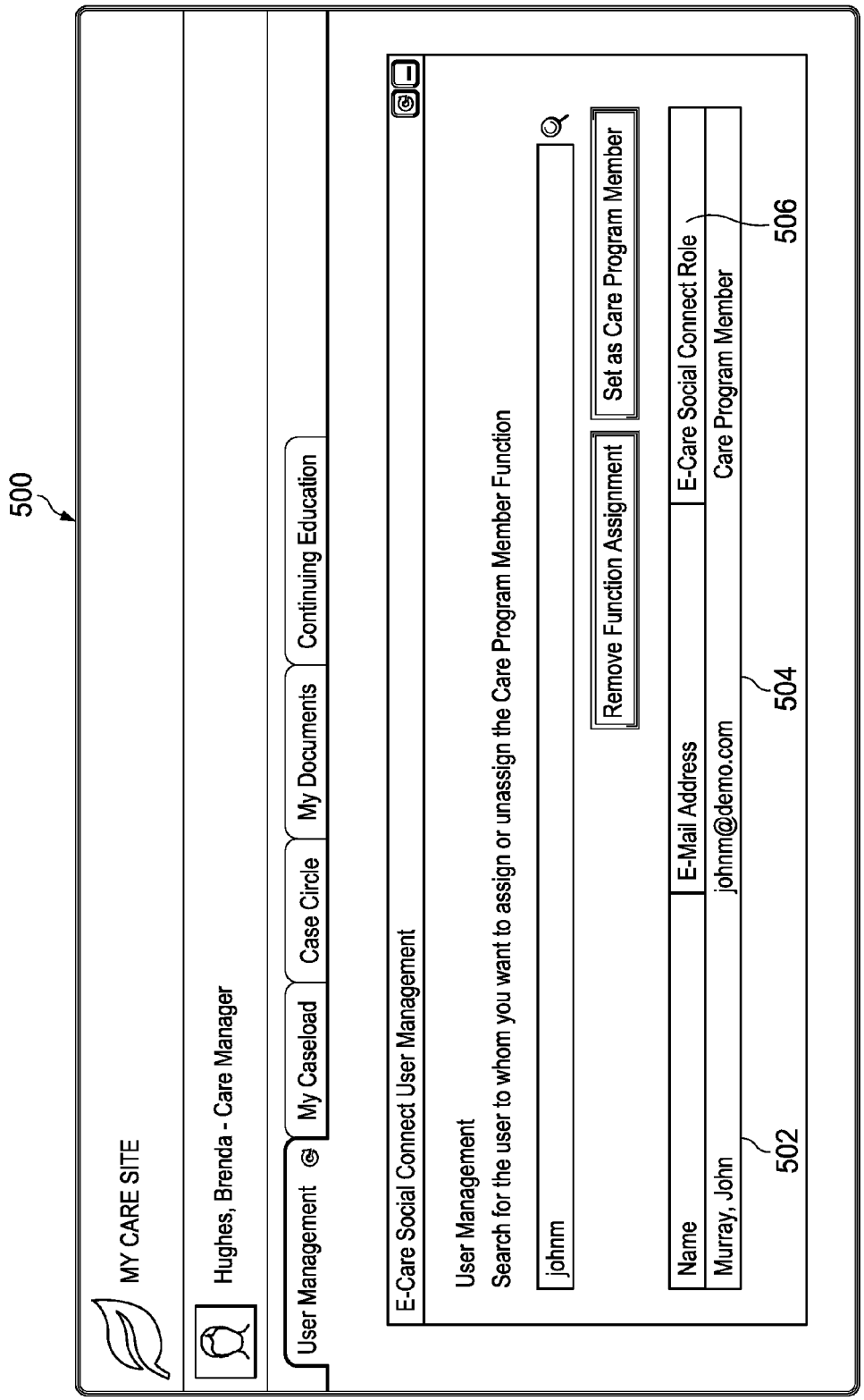
FIG. 5 is an example of a first user interface to manage users of the workspace.

In the example user interface described above, the computer system 150 presented the user with the multiple workspaces in which the user can access the computer system 150 and received a selection of one of the workspaces from the user. In some implementations, the computer system 150 can automatically determine the workspace without user intervention. The computer system 150 can determine the workspace based on factors including a geographical location from which the user accesses the computer system 150 or the time of day. For example, based on an Internet Protocol (IP) address of the computer system using which the user accesses the computer system 150 that provides the workspaces, the computer system 150 can determine that the user is accessing the computer system 150 from the user's home. The computer system 150 can determine that, when the user accesses the computer system 150 from home, the user is more likely to access a personal account, for example, in a "Care Program Receiver" role, than a professional account, for example, in a "Care Program Provider" role. In response, the computer system 150 can automatically grant the user access to the workspace that includes the subset of the content associated with the "Care Program Receiver" role. In another example, if the computer system 150 determines that the user's geographical location is the user's office and the time of day is early afternoon on a weekday, then the computer system 150 can determine that the user is more likely to access the professional account. In response, the computer system 150 can automatically grant the user access to the workspace that includes the subset of the content associated with the "Care Program Provider" role. In some implementations, the computer system 150 can request the user to specify a default workspace which the user will access when accessing the computer system that provides the workspaces. The computer system 150 can grant the user access to the workspace that includes the subset of content associated with the default role when the user accesses the workspace FIG. 5 is an example of a first user interface 500 to manage users of the workspaces. The user interface 500 can be implemented as computer instructions stored on a computer-readable medium (for example, the computer-readable medium 152) and executable by data processing apparatus (for example, the data processing apparatus 154). For example, the user interface 500 can be implemented by the computer system 150. The user interface 500 can be a user management webpage that a care manager, for example, an administrator of the workspace, can use to manage users of the workspace. The user interface 500 can include a "Name" portion 502, a "Contact Information" portion 504, and a "Role" portion 506. For example, the "Name" portion 502 can include a name of the user ("Murray, John"), the "Contact Information" portion 504 can include an e-mail address for the user (johnm@demo.com), and the "Role" portion 506 can include the user's role ("Care Program Member"). The manager of the webpage can add, remove, or change information associated with the users of the workspace using the user interface 500.

Figure 6:
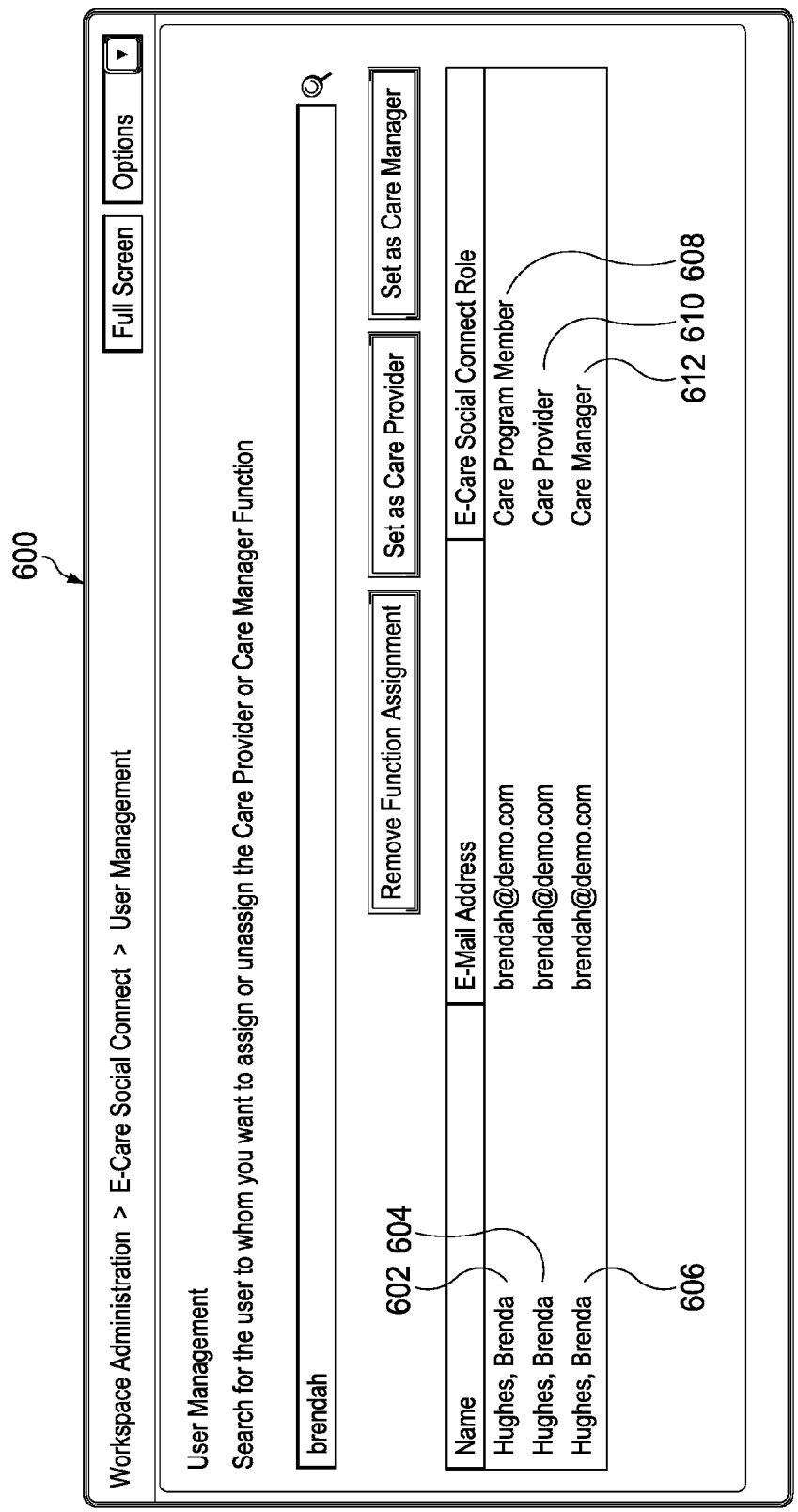
FIG. 6 is an example of a second user interface to manage users of the workspace.

FIG. 6 is an example of a second user interface 600 to manage users of the workspaces. The user interface 600 can be implemented as computer instructions stored on a computer-readable medium (for example, the computer-readable medium 152) and executable by data processing apparatus (for example, the data processing apparatus 154). For example, the user interface 600 can be implemented by the computer system 150. The user interface 600 can be another user management webpage that a care manager, for example, an administrator of the workspace, can use to manage users of the workspace. The user interface 600 displays the same user entitled "Hughes, Brenda" having three different roles in one or more workspaces—a "Care Program Member" role, a "Care Provider" role and a "Care Member" role. In some implementations, the computer system 150 can display the user's name and the roles in respective rows of a table. For example, in a column entitled "Name," the computer system 150 can display the user's name in a first portion 602 of a first row, a second portion 604 of a second row, and a third portion 606 of a third row. In the first row, the computer system 150 can display the user's first role ("Care Program Member") in a fourth portion 608. In the second row, the computer system 150 can display the user's second role ("Care Provider") in a fifth portion 610. In the third row, the computer system 150 can display the user's third role ("Care Manager") in a sixth portion 612. Each portion in the user interface 600 can be editable. The manager of the workspace can add, delete, or change information about each user and each user's role by editing a portion in the user interface 600.

Figure 7:
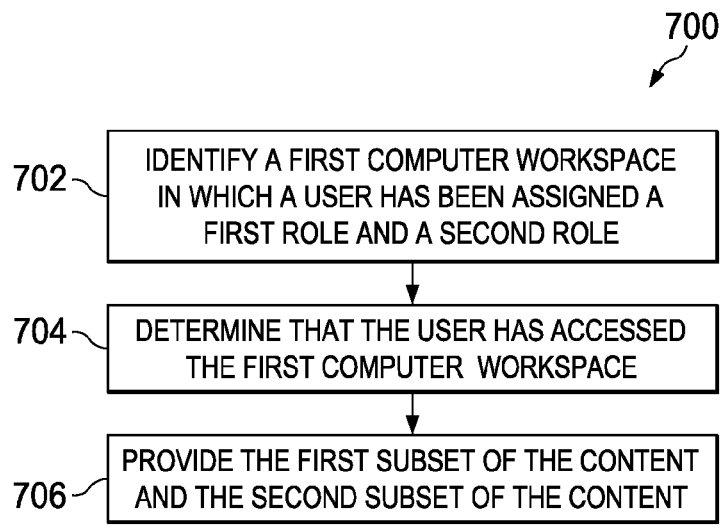
FIG. 7 is a flowchart of an example process to provide multiple roles in the workspace.

FIG. 7 is a flowchart of an example process 700 to provide multiple roles in the workspace. The user's role in the workspace, as used in this disclosure, can be one of several special roles that are applicable to a user in particular contexts of the workspace. This is in contrast to system-wide roles that are applicable anywhere in the system. The process 700 can be implemented as computer instructions stored on computer-readable media (for example, the computer-readable medium 152) and executable by data processing apparatus (for example, data processing apparatus 154). For example, the process 700 can be implemented by the computer system 150. At 702, a first computer workspace in which a user has been assigned a first role and a second role is identified. Each of the first computer workspace and the second computer workspace provides content. At least a portion of the content is accessible by the user. The first role defines a first subset of the content that is accessible by the user. At 704, it is determined that the user has accessed the first computer workspace in which the user has been assigned the first role and the second role. At 706, the first subset of the content and the second subset of the content is provided to the user in response to determining that the user has accessed the first computer workspace.

Figure 8:
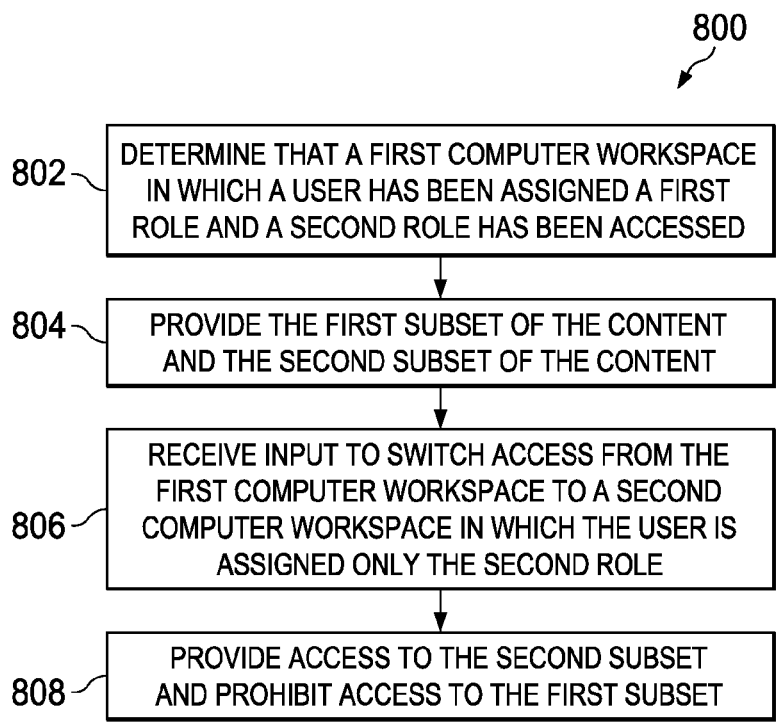
FIG. 8 is a flowchart of an example process to provide access to content in different workspaces.

FIG. 8 is a flowchart of an example process 800 to provide access to content in different workspaces. The process 800 can be implemented as computer instructions stored on computer-readable media (for example, the computer-readable medium 152) and executable by data processing apparatus (for example, data processing apparatus 154). For example, the process 800 can be implemented by the computer system 150. At 802, it be determined that a first computer workspace in which a user has been assigned a first role and a second role has been accessed. The first computer workspace provides content. At least a portion of the content is accessible to the user. The first role defines a first subset of the content that is accessible by the user. The second role defines a second subset of the content that is accessible by the user.

At 804, the first subset of the content and the second subset of the content can be provided in response to determining the access of the first computer workspace. At 806, input to switch access from the first computer workspace to a second computer workspace that is different from the first computer workspace can be received. The user is assigned only the second role in the second computer workspace. At 808, the second subset of the content can be provided and access to the first subset of the content can be prohibited in response to receiving the input to switch the access from the first computer workspace to the second computer workspace.

In general, the EWS server 102 is a server that stores a content provider manager 108, a role assignment engine 109, a search engine 110, and a rule engine 111 where at least a portion of the content provider manager 108, the role assignment engine 109, the search engine 110, or the rule engine 111 (or combinations of them) is executed using requests or responses (or both) sent from or to the computer system 150. In some implementations, the EWS server 102 may store multiple content provider managers 108, rule assignment engines 109, search engines 110, or rule engines 111 (or combinations of them). In some implementations, the EWS server 102 may be a dedicated server meant to store and execute only a single content provider manager 108, role assignment engine 109, search engine 110, or rule engine 111 (or combinations of them). In some implementations, the EWS server 102 may comprise a web server, where content provider manager 108, the role assignment engine 109, the search engine 110, or the rule engine 111 (or combinations of them) represents one or more web-based applications accessed and executed by the computer system 150 or directly at the EWS server 102 to perform the programmed tasks or operations of the content provider manager 108, the role assignment engine 109, the search engine 110, or the rule engine 111 (or combinations of them). The EWS server 102 can include an application programming interface (API) 112 or a service layer 113 (or both) through which the various components of the EWS server 102 can interface with each other.

The EWS server 102 includes an interface 104 for communicating with other systems in a distributed environment (i.e., the interconnected computer systems). Generally, the interface 104 comprises logic encoded in software or hardware (or both) in a suitable combination and operable to communicate with one or more wired or wireless networks 180, such as, the Internet. The EWS server 102 includes a processor 106 which executes instructions and manipulates data to perform the operations of the EWS server 102. Specifically, the processor 106 executes the functionality required to receive and respond to requests from the computer system 150, one or more of the interconnected computer systems, and the role assignment engine 109. The EWS server 102 also includes a memory 107 that holds data for the EWS server 102. In some implementations, the memory 107 includes an EWS 116, an EWS page 117, a module 118, module content 119, a module template 120, a module gallery 121, a rule 122, and a user property 123.

The EWS is a central repository of knowledge. EWS generation may be performed either at design-time or run-time and may be based upon, for example, EWS properties, an EWS owner profile, EWS viewer properties, other suitable values or combinations thereof. For example, the EWS owner profile may include age, address, medical profile, etc. The EWS viewer profile may include role, relation to the EWS owner, location, etc. In some implementations, the EWS is associated with a context. For example, the EWS may be associated with a specific user, for example a particular patient, and a support group associated with the patient, for example, the patient's doctor, friends and family, etc. The EWS may be either personal or shared. The personal EWS is a private area where a single user can maintain personal content on a particular EWS page not accessible by other EWS users. A shared EWS is an area where multiple EWS users, for example the support group or friends and family of the heart patient, can access shared EWS pages. A shared EWS is assigned a role/permission policy and each EWS user may be provided a role and associated permission in the shared EWS. Roles may be, for example, workspace owner, workspace manager, workspace member or combinations of them. Associated permissions may be, for example, the ability to create, rename, or delete EWS pages and view or update particular content associated with EWS pages or specific modules associated with the EWS pages. In some implementations, EWS users may have multiple permission levels/roles. In some implementations, users can also customize the EWS with different layouts, branding, and themes. In some implementations, an EWS instance is created from a reusable EWS template. An EWS template has the same or similar structure as an EWS and is an EWS associated with a template tag but not an actual EWS instance. If a new instance of an EWS is created based on an EWS template, the EWS template is copied and used as the base for the EWS instance.

An enterprise portal (EP) (also known as an enterprise information portal (EIP) or a corporate portal) is a framework for integrating information, people, and processes across organizational boundaries. An EP can provide a secure unified access point, for example, in the form of a web-based user interface. The EP can be designed to aggregate and personalize information through application-specific portals. The EP can be a de-centralized content contribution and content management system, which maintains updated information almost all the time. Using a web browser, an enterprise portal user can begin work after having been authenticated in the EP. In this manner, the EP can offer a single point of access to information, enterprise applications, and services both inside and outside an organization. EPs can present information from diverse sources in a unified and structured way, and provide additional services, such as dashboards, an internal search engine, e-mail, news, navigation tools, and various other features. EPs can be used by enterprises for providing their employees, customers, and possibly additional users with a consistent look and feel, and access control and procedures for multiple applications, which otherwise would have been separate entities altogether.

Implementations of the subject matter and the operations described in this disclosure can be implemented in digital electronic circuitry, or in computer software, firmware, or hardware, including the structures disclosed in this disclosure and their structural equivalents, or in combinations of one or more of them. Implementations of the subject matter described in this disclosure can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, for example, a machine-generated electrical, optical, or electromagnetic signal that is generated to encode information for transmission to suitable receiver apparatus for execution by a data processing apparatus. A computer storage medium, for example, the computer-readable medium, can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical and/or non-transitory components or media (for example, multiple CDs, disks, or other storage devices).

In some implementations, the operations described in this disclosure can be implemented as a hosted service provided on a server in a cloud computing network. For example, the computer-readable storage media can be logically grouped and accessible within a cloud computing network. Servers within the cloud computing network can include a cloud computing platform for providing cloud-based services. The terms "cloud," "cloud computing," and "cloud-based" may be used interchangeably as appropriate without departing from the scope of this disclosure. Cloud-based services can be hosted services that are provided by servers and delivered across a network to a client platform to enhance, supplement, or replace applications executed locally on a client computer. The system can use cloud-based services to quickly receive software upgrades, applications, and other resources that would otherwise require a lengthy period of time before the resources can be delivered to the system.

The operations described in this disclosure can be implemented as operations performed by a data processing apparatus on data stored on one or more computer-readable storage devices or received from other sources. The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, for example, an FPGA (field programmable gate array) or an ASIC (application-specific integrated circuit). The apparatus can also include, in addition to hardware, code that creates an execution environment for the computer program in question, for example, code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (for example, one or more scripts stored in a markup language document), in a single file dedicated to the program in question, or in multiple coordinated files (for example, files that store one or more modules, sub-programs, or portions of code). A computer program can be deployed to be executed on one computer or on multiple computers that are located at one site or distributed across multiple sites and interconnected by a communication network.

The processes and logic flows described in this disclosure can be performed by one or more programmable processors executing one or more computer programs to perform actions by operating on input data and generating output. The processes and logic flows can also be performed by, and apparatus can also be implemented as, special purpose logic circuitry, for example, an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, for example, magnetic, magneto-optical disks, or optical disks. However, a computer need not have such devices. Moreover, a computer can be embedded in another device, for example, a mobile telephone, a personal digital assistant (PDA), a mobile audio or video player, a game console, a Global Positioning System (GPS) receiver, or a portable storage device (for example, a universal serial bus (USB) flash drive), to name just a few. Devices suitable for storing computer program instructions and data include all forms of non-volatile memory, media and memory devices, including by way of example semiconductor memory devices, for example, EPROM, EEPROM, and flash memory devices; magnetic disks, for example, internal hard disks or removable disks; magneto-optical disks; and CD-ROM and DVD-ROM disks. The processor and the memory can be supplemented by, or incorporated in, special purpose logic circuitry.

To provide for interaction with a user, implementations of the subject matter described in this disclosure can be implemented on a computer having a display device, for example, a CRT (cathode ray tube) or LCD (liquid crystal display) monitor, for displaying information to the user, and a keyboard, a pointing device, for example, a mouse or a trackball, or a microphone and speaker (or combinations of them) by which the user can provide input to the computer. Other kinds of devices can be used to provide for interaction with a user as well; for example, feedback provided to the user can be any form of sensory feedback, for example, visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Implementations of the subject matter described in this disclosure can be implemented in a computing system that includes a back-end component, for example, as a data server, or that includes a middleware component, for example, an application server, or that includes a front-end component, for example, a client computer having a graphical user interface or a Web browser through which a user can interact with an implementation of the subject matter described in this disclosure, or any combination of one or more such back-end, middleware, or front-end components. The components of the system can be interconnected by any form or medium of digital data communication, for example, a communication network. Examples of communication networks include a local area network ("LAN") and a wide area network ("WAN"), an inter-network (for example, the Internet), and peer-to-peer networks (for example, ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some implementations, a server transmits data (for example, an HTML page) to a client device (for example, for purposes of displaying data to and receiving user input from a user interacting with the client device). Data generated at the client device (for example, a result of the user interaction) can be received from the client device at the server.

While this disclosure contains many specific implementation details, these should not be construed as limitations on the scope of any implementations or of what may be claimed, but rather as descriptions of features specific to particular implementations of particular implementations. Certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A method performed by data processing apparatus, the method comprising:
    determining that a user has accessed a computer system, the computer system providing a plurality of computer workspaces, each computer workspace associated with a corresponding context, each context including at least one of a geographical location from which the user accesses the computer system or a time of day when the user accesses the computer system, each computer workspace providing content, at least a portion of the content being accessible by the user;
    identifying a current context associated with the user access of the computer system, the current context identifying at least one of a current geographical location from which the user accesses the computer system or a current time of day when the user accesses the computer system;
    based on the current context associated with the user access, identifying, automatically and without user intervention, a first computer workspace from the plurality of computer workspaces satisfying the identified current context, wherein the user has been assigned a first role and a second role in the first computer workspace and assigned only the second role in a second computer workspace that is different from the first computer workspace, the first role defining a first subset of the content that is accessible by the user, and the second role defining a second subset of the content that is accessible by the user, the second workspace in the plurality of computer workspaces;
    in response to identifying the first computer workspace, automatically and without user intervention, granting access to the user for the identified first computer workspace;
    in response to a request from the user for the first computer workspace received while accessing the computer system in the current context that matches the corresponding context of the first computer workspace and after the user has been granted access to the first computer workspace, providing the first subset of the content and the second subset of the content to the user; and
    in response to the user accessing the computer system in a new context that matches the corresponding context of the second computer workspace, providing only the second subset of the content to the user.

2. The method of claim 1, wherein the content includes data and computer-implemented applications accessible by the user.

3. The method of claim 1, further comprising persisting a first relationship and a second relationship between the user and the first computer workspace, wherein the first relationship and the second relationship are based on the first role and the second role, respectively.

4. The method of claim 3, wherein persisting the first relationship comprises tagging the first relationship with a string of characters that represents the first role.

5. The method of claim 3, wherein persisting the first relationship comprises persisting the first relationship in the first computer workspace.

6. The method of claim 3, wherein persisting the second relationship comprises persisting the second relationship in a user account associated with the user.

7. The method of claim 3, wherein persisting the first relationship comprises associating an identifier to identify the user and an identifier to identify the first computer workspace with the first role.

8. The method of claim 1, further comprising receiving a selection of the first computer workspace in a user interface that displays the first computer workspace and the second computer workspace.

9. The method of claim 8, further comprising, in response to receiving a selection of the second computer workspace in the user interface, displaying a different user interface that provides only the second subset of the content.

10. The method of claim 8, comprising:
    receiving, in the user interface, an input to switch from the first computer workspace to the second computer workspace; and
    displaying a different user interface that displays the second subset of content in response to receiving the input to switch.

11. The method of claim 1, wherein the first role is assigned based on a business role of the user in the context of the first computer workspace.

12. A non-transitory computer-readable medium storing instructions executable by data processing apparatus to perform operations including:
    determining that a user has accessed a computer system, the computer system providing a plurality of computer workspaces, each computer workspace associated with a corresponding context, each context including at least one of a geographical location from which the user accesses the computer system or a time of day when the user accesses the computer system, each computer workspace providing content, at least a portion of the content being accessible by the user;

identifying a current context associated with the user access of the computer system, the current context identifying at least one of a current geographical location from which the user accesses the computer system or a current time of day when the user accesses the computer system;

based on the current context associated with the user access, identifying, automatically and without user intervention, a first computer workspace from the plurality of computer workspaces satisfying the identified current context, wherein the user has been assigned a first role and a second role in the first computer workspace and assigned only the second role in a second computer workspace that is different from the first computer workspace, the first role defining a first subset of the content that is accessible by the user, and the second role defining a second subset of the content that is accessible by the user, the second workspace in the plurality of computer workspaces;

in response to identifying the first computer workspace, automatically and without user intervention, granting access to the user for the identified first computer workspace;

in response to a request from the user for the first computer workspace received while accessing the computer system in the current context that matches the corresponding context of the first computer workspace and after the user has been granted access to the first computer workspace, providing the first subset of the content and the second subset of the content to the user; and in response to the user accessing the computer system in a new context that matches the corresponding context of the second computer workspace, providing only the second subset of the content to the user.

13. The medium of claim 12, the operations further comprising persisting a first relationship and a second relationship between the user and the first computer workspace, wherein the first relationship and the second relationship are based on the first role and the second role, respectively.

14. The medium of claim 13, wherein persisting the first relationship comprises tagging the first relationship with a string of characters that represents the first role.

15. The medium of claim 13, wherein persisting the first relationship comprises persisting the first relationship in the first computer workspace.

16. The medium of claim 13, wherein persisting the second relationship comprises persisting the second relationship in a user account associated with the user.

17. A system comprising:

data processing apparatus; and a computer-readable medium storing instructions executable by the data processing apparatus to perform operations comprising:

determining that a user has accessed a computer system, the computer system providing a plurality of computer workspaces including a first computer workspace and a second computer workspace, each computer workspace associated with a corresponding context, each context including at least one of a geographical location from which the user accesses the computer system or a time of day when the user accesses the computer system, each computer workspace providing content, at least a portion of the content being accessible by the user;

identifying a current context associated with the user access of the computer system, the current context identifying at least one of a current geographical location from which the user accesses the computer system or a current time of day when the user accesses the computer system;

based on the current context associated with the user access, identifying, automatically and without user intervention, the first computer workspace satisfying the identified current context, wherein the user has been assigned a first role and a second role in the first computer workspace, the first role defining a first subset of the content that is accessible by the user, and the second role defining a second subset of the content that is accessible by the user;

in response to identifying the first computer workspace, automatically and without user intervention, granting access to the user for the identified first computer workspace;

in response to a request from the user for the first computer workspace received while accessing the computer system in the current context that matches the corresponding context of the first computer workspace and after the user has been granted access to the first computer workspace, providing the first subset of the content and the second subset of the content to the user;

receiving input to switch from the first computer workspace to the second computer workspace that is different from the first computer workspace, the user is assigned only the second role in the second computer workspace; and providing the second subset of the content and prohibiting access to the first subset of the content in response to receiving the input to switch from the first computer workspace to the second computer workspace and the user accessing the computer system in a new context that matches the corresponding context of the second computer workspace.

* * * * *